(12) United States Patent
Franke et al.

(10) Patent No.: US 11,667,657 B2
(45) Date of Patent: Jun. 6, 2023

(54) DIPHOSPHITES BASED ON CIS-BUTENE-1,4-DIOL

(71) Applicant: EVONIK OPERATIONS GMBH, Essen (DE)

(72) Inventors: Robert Franke, Marl (DE); Detlef Selent, Rostock (DE); Armin Börner, Rostock (DE); Anna Chiara Sale, Recklinghausen (DE)

(73) Assignee: EVONIK OPERATIONS GMBH, Essen (DE)

( * ) Notice: Subject to any disclaimer, the term of this patent is extended or adjusted under 35 U.S.C. 154(b) by 0 days.

(21) Appl. No.: 17/402,905

(22) Filed: Aug. 16, 2021

(65) Prior Publication Data

US 2022/0056060 A1    Feb. 24, 2022

(30) Foreign Application Priority Data

Aug. 18, 2020   (EP) .................................... 20191440

(51) Int. Cl.
*C07C 45/50*   (2006.01)
*C07F 9/6574*   (2006.01)
*B01J 31/18*   (2006.01)

(52) U.S. Cl.
CPC .......... *C07F 9/65746* (2013.01); *B01J 31/185* (2013.01); *B01J 2531/004* (2013.01); *B01J 2531/821* (2013.01); *B01J 2531/822* (2013.01); *B01J 2531/827* (2013.01); *B01J 2531/845* (2013.01)

(58) Field of Classification Search
CPC ...... C07C 45/50; C07F 9/65745; B01J 31/185
See application file for complete search history.

(56) References Cited

FOREIGN PATENT DOCUMENTS

| CN | 105801625 A | 7/2016 |
|---|---|---|
| WO | 2006/082054 A1 | 8/2006 |

OTHER PUBLICATIONS

European Search Report dated Jan. 25, 2021 for European Patent Application No. 20191440.5 (8 pages in German with translation).
R. Franke, et al. "Applied Hydroformylation" Chemical Reviews, 2012, pp. 5675-5732.

*Primary Examiner* — Sikarl A Witherspoon
(74) *Attorney, Agent, or Firm* — Smith, Gambrell & Russell, LLP

(57) ABSTRACT

New diphosphites based on cis-butene-1,4-diol.

13 Claims, No Drawings

DIPHOSPHITES BASED ON CIS-BUTENE-1,4-DIOL

The invention relates to new diphosphites based on cis-butene-1,4-diol.

Phosphorus-containing compounds play a crucial role as ligands in a multitude of reactions, e.g. in hydrogenation, in hydrocyanation and also in hydroformylation.

The reactions between olefin compounds, carbon monoxide and hydrogen in the presence of a catalyst to give the aldehydes with one carbon atom more are known as hydroformylation or the oxo process. Catalysts used in these reactions are frequently compounds of the transition metals of group VIII of the periodic table of the elements. Known ligands are, for example, compounds from the phosphine, phosphite and phosphonite classes, each containing trivalent phosphorus $P^{III}$. A good overview of the situation on the hydroformylation of olefins can be found in R. Franke, D. Selent, A. Börner, "Applied Hydroformylation", Chem. Rev., 2012, DOI:10.1021/cr3001803.

CN 105801625A describes a method for preparing bidentate phosphite ligands and the use thereof in the Buchwald-Hartwig reaction. The ligands exhibit increased reaction activity in the Pd-catalysed Buchwald-Hartwig reaction.

The technical object of the invention is to provide new ligands that exhibit increased selectivity in the hydroformylation of olefins.

The object is achieved by a compound according to claim 1.

Compound of the structure (I) or (II):

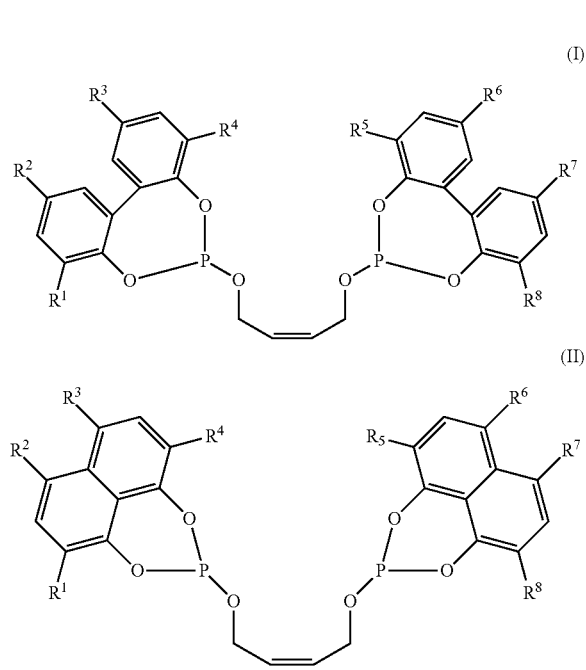

where $R^1, R^2, R^3, R^4, R^5, R^6, R^7, R^8$ are selected from: —H, —($C_1$-$C_{12}$) alkyl, —O—($C_1$-$C_{12}$) alkyl, and the radicals $R^1$, $R^2, R^3, R^4, R^5, R^6, R^7, R^8$ are not all simultaneously —$^iBu$.

In one embodiment, $R^1, R^4, R^5, R^8$ are selected from: —H, —($C_1$-$C_{12}$) alkyl.

In one embodiment, the radicals $R^1, R^4, R^5, R^8$ are not all simultaneously —$^iBu$.

In one embodiment, the radicals $R^1, R^4, R^5, R^8$ are not —$^iBu$.

In one embodiment, at least one of the radicals $R^1, R^4, R^5, R^8$ is —H.

In one embodiment, $R^1, R^4, R^5, R^8$ are —H.

In one embodiment, $R^2, R^3, R^6, R^7$ are selected from: —H, —O—($C_1$-$C_{12}$) alkyl.

In one embodiment, at least one of the radicals $R^2, R^3, R^6, R^7$ is —H.

In one embodiment, $R^2, R^3, R^6, R^7$ are —H.

In one embodiment, the compound has the structure (I).

In one embodiment, the compound has the structure (1):

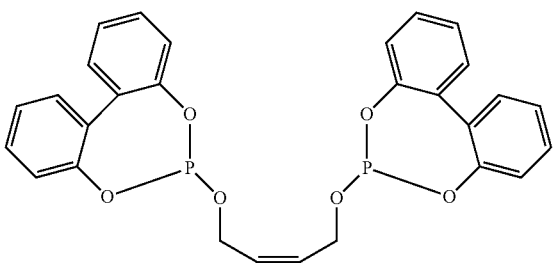

In one embodiment, the compound has the structure (II).
In one embodiment, the compound has the structure (2):

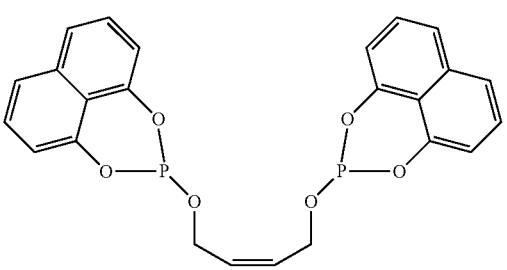

As well as the compound per se, the use thereof for catalysis of a hydroformylation reaction is also claimed.

Use of an above-described compound in a ligand-metal complex for catalysis of a hydroformylation reaction.

Additionally claimed is a process in which the above-described compound is used as a ligand.

Process comprising the process steps of:
a) initially charging an olefin,
b) adding an above-described compound and a substance containing a metal selected from: Rh, Ru, Co, Ir,
c) feeding in $H_2$ and CO,
d) heating the reaction mixture from steps a) to c), with conversion of the olefin to an aldehyde.

In a preferred embodiment, the metal is Rh.

The ligands can also be used in excess here and it is not automatically the case that each ligand is present in bound form as a ligand-metal complex; it may instead be present in the reaction mixture as the free ligand.

The reaction is carried out under customary conditions.

Preference is given to a temperature of 60° C. to 160° C. and a pressure of 5 to 70 bar. Particular preference is given to a temperature of 70° C. to 140° C. and a pressure of 15 to 60 bar.

The reactants for the hydroformylation in the process of the invention are olefins or mixtures of olefins, especially monoolefins having 2 to 24, preferably 3 to 16 and more preferably 3 to 12 carbon atoms, and having terminal or internal C—C double bonds, for example 1-propene, 1-butene, 2-butene, 1- or 2-pentene, 2-methyl-1-butene, 2-methyl-2-butene, 3-methyl-1-butene, 1-, 2- or 3-hexene, the $C_6$ olefin mixture obtained in the dimerization of propene (dipropene), heptenes, 2- or 3-methyl-1-hexenes, octenes, 2-methylheptenes, 3-methylheptenes, 5-methyl-2-heptene, 6-methyl-2-heptene, 2-ethyl-1-hexene, the $C_8$ olefin mixture obtained in the dimerization of butenes (di-n-butene, diisobutene), nonenes, 2- or 3-methyloctenes, the $C_9$ olefin mixture obtained in the trimerization of propene (tripropene), decenes, 2-ethyl-1-octene, dodecenes, the $C_{12}$ olefin mixture obtained in the tetramerization of propene or the trimerization of butenes (tetrapropene or tributene), tetradecenes, hexadecenes, the $C_{16}$ olefin mixture obtained in the tetramerization of butenes (tetrabutene), and olefin mixtures having different numbers of carbon atoms (preferably 2 to 4) produced by cooligomerization of olefins.

The process of the invention using the ligands of the invention can be used for the hydroformylation of α-olefins, terminally branched, internal and internally branched olefins.

The invention shall be illustrated in detail hereinbelow with reference to exemplary embodiments.

Work Procedures
General Analysis

All the preparations that follow were carried out under inert gas using standard Schlenk techniques. The solvents were dried before use over suitable drying agents.

The products were characterized by NMR spectroscopy. Chemical shifts (δ) are reported in ppm. The $^{31}P$ NMR signals were referenced as follows: $SR^{31}P=SR^1H*(BF^{31}P/BF^1H)=SR^1H*0.4048$.

Synthesis of (Z)-1,4-bis(dibenzo[d,f][1,3,2]dioxaphosphepin-6-yloxy)but-2-ene (1)

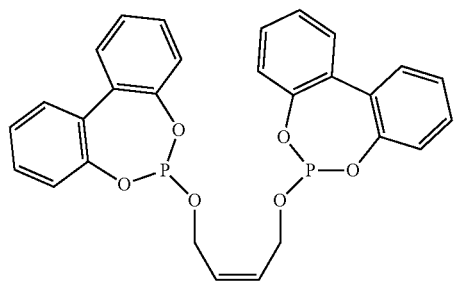

(1)

To a mixture of cis-butene-1,4-diol (0.206 g; 2.334 mmol) and triethylamine (1.0 ml) in toluene (10 ml) cooled to 0° C. is added dropwise with stirring a solution of 6-chlorodibenzo[d,f][1,3,2]dioxaphosphepine (1.253 g; 5.0 mmol) in toluene (7 ml). The mixture is allowed to warm to room temperature, stirred overnight, filtered, and the filtrate is concentrated to dryness. The viscous residue is dried for 4 h at 50° C./0.1 mbar and then purified by column chromatography (hexane/dichloromethane=1:1; $R_f$=0.5). Yield: 0.733 g (1.42 mmol; 61%). Elemental analysis (calculated for $C_{28}H_{22}O_6P_2$=516.42 g/mol): C=65.02 (65.12); H=4.22 (4.29); P=11.96 (12.00)%.

ESI-TOF HRMS, m/z=539.0787; [M+Na⁺]; calculated m/z=539.0784.

$^{31}P$ NMR ($CD_2Cl_2$): 139.4 (s) ppm.
$^1H$ NMR ($CD_2Cl_2$): 4.49 (m, 4H); 5.79 (m, 2H); 7.21-7.56 (m, 16H) ppm.
$^{13}C$ NMR ($CD_2Cl_2$): 60.1 (d, $^2J_{CP}$=5.7 Hz); 121.8; 125.2; 128.8; 129.4; 130.0; 130.9; 149.8 ppm.

Synthesis of (Z)-1,4-bis(naphtho[1,8-de][1,3,2]dioxaphosphinin-2-yloxy)but-2-ene (2)

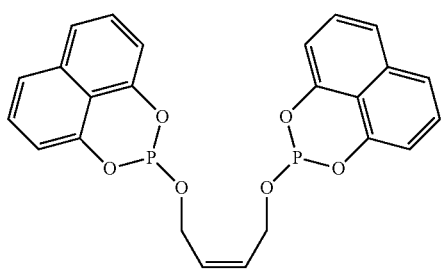

(2)

To a mixture of cis-butene-1,4-diol (0.230 g; 2.613 mmol) and triethylamine (1.14 ml) in toluene (5 ml) cooled to 0° C. is added dropwise with stirring a solution of 2-chloronaphtho[1,8-de][1,3,2]dioxaphosphinine (1.232 g; 5.487 mmol) in toluene (16 ml). The mixture is allowed to warm to room temperature, stirred overnight, filtered, and the filtrate is concentrated to dryness. The residue is taken up in acetonitrile (9 ml). Filtration, concentration and drying affords a highly viscous product. Yield: 0.938 g (2.02 mmol; 77%).

Elemental analysis (calculated for $C_{24}H_{18}O_6P_2$=464.35 g/mol): C=62.16 (62.08); H=3.95 (3.91); P=13.45 (13.34)%.

ESI-TOF HRMS, m/z=487.0480; [M+Na⁺]; calculated m/z=487.0471.

$^{31}P$ NMR ($CD_2Cl_2$): 112.8 (s) ppm.
$^1H$ NMR ($CD_2Cl_2$): 4.34 (m, 4H); 5.52 (m, 2H); 6.96 (m, 4H); 7.43 (m, 4H); 7.55 (m, 4H) ppm.
$^{13}C$ NMR ($CD_2Cl_2$): 59.5 (d, $^2J_{CP}$=15.2 Hz); 111.9; 116.5 (d, $^2J_{CP}$=14.3 Hz); 122.1; 127.3; 128.8; 135.0; 144.2 ppm.

Synthesis of (Z)-1,4-bis((4,4,5,5-tetraphenyl-1,3,2-dioxaphospholan-2-yl)oxy)but-2-ene (3 (Comparative Ligand)

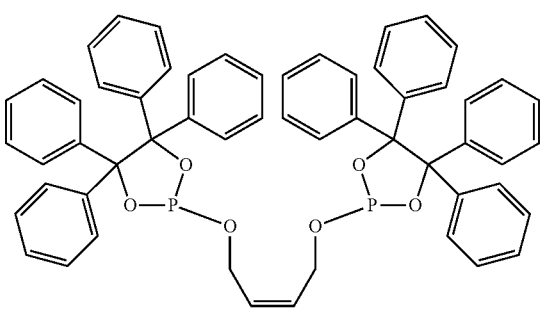

(3)

To a mixture of cis-butene-1,4-diol (0.091 g; 1.032 mmol) and triethylamine (0.45 ml) in toluene (2 ml) cooled to 0° C. is added dropwise with stirring a solution of 2-chloro-4,4,5,5-tetraphenyl-1,3,2-dioxaphospholane (0.979 g; 2.271 mmol) in toluene (5 ml). The mixture is allowed to warm to room temperature, stirred overnight and filtered through a frit covered with silica gel and then evaporated to dryness. The solid obtained is dried for 4.5 h at 0.1 mbar/50° C. and then recrystallized from hot acetonitrile. Yield: 0.375 g (0.428 mmol; 41%).

Elemental analysis (calculated for $C_{56}H_{46}O_6P_2$=876.92 g/mol): C=76.68 (76.70); H=5.15 (5.29); P=7.03 (7.06) %.

ESI-TOF HRMS, m/z=899.2689; [M+Na$^+$]; calculated m/z=899.2667.

$^{31}$P NMR (CD$_2$Cl$_2$): 147.6 (s) ppm.

$^1$H NMR (CD$_2$Cl$_2$): 4.14 (m, 4H); 5.21 (m, 2H); 7.07-7.25 (m, 32H); 7.49-7.53 (m, 8H) ppm.

$^{13}$C NMR (CD$_2$Cl$_2$): 59.0 (d, $^2J_{CP}$=24.3 Hz); 94.3 (d, $^2J_{CP}$=8.3 Hz); 127.0 (s, br); 127.2 (s); 128.8 (s, br); 129.7 (s); 142.3 (m); 142.9 (s) ppm.

Catalysis Experiments

The hydroformylation was carried out in a 200 ml autoclave from Premex Reactor AG, Lengau, Switzerland equipped with pressure-retaining valve, gas flowmeter, sparging stirrer and pressure pipette. To minimize the influence of moisture and oxygen, the toluene used as solvent was purified in a Pure Solv. MD-7 System and stored under argon. The olefin 1-octene used as substrate (Aldrich) was heated at reflux over sodium and distilled under argon. Toluene solutions of the catalyst precursor and of the ligand were mixed in an autoclave under an argon atmosphere. [(acac)Rh(COD)] (Umicore, acac=acetylacetonate anion, COD=1,5-cyclooctadiene) was used as catalyst precursor. The autoclave was heated while stirring (1500 rpm) at an overall gas pressure (syngas: Linde; H$_2$ (99.999%):CO (99.997%)=1:1) of 42 bar for a final pressure of 50 bar. On reaching the reaction temperature, the syngas pressure was increased to 48.5 bar and the olefin was pressure-injected into the autoclave by means of a pressure pipette set to an overpressure of approx. 3 bar. The reaction was carried out at a constant pressure of 50 bar (dosed-loop pressure controller from Bronkhorst, the Netherlands) over 4 h. At the end of the reaction time, the autoclave was cooled to room temperature, depressurized while stirring and flushed with argon, 1 ml of each reaction mixture was removed immediately after the stirrer had been switched off, diluted with 10 ml of pentane and analysed by gas chromatography: HP 5890 Series II plus, PONA, 50 m×0.2 mm×0.5 µm.

Results of the Catalysis Experiments

[Rh]: 100 ppm, Rh:L=1:2, p: 50 bar, T: 80° C.; t: 4 h

TABLE 1

| Hydroformylation of 1-octene | | |
|---|---|---|
| Entry | Ligand | Selectivity [%] |
| 1 | 1* | 71.9 |
| 2 | 2* | 69.7 |
| 3 | 3 | 51.4 |

*inventive compound

The compounds of the invention (1) and (2) achieved an increase in selectivity compared with the comparative ligand (3).

The experiments carried out demonstrate that the stated object is achieved by the compounds of the invention.

The invention claimed is:

1. A compound having structure (I) or (II):

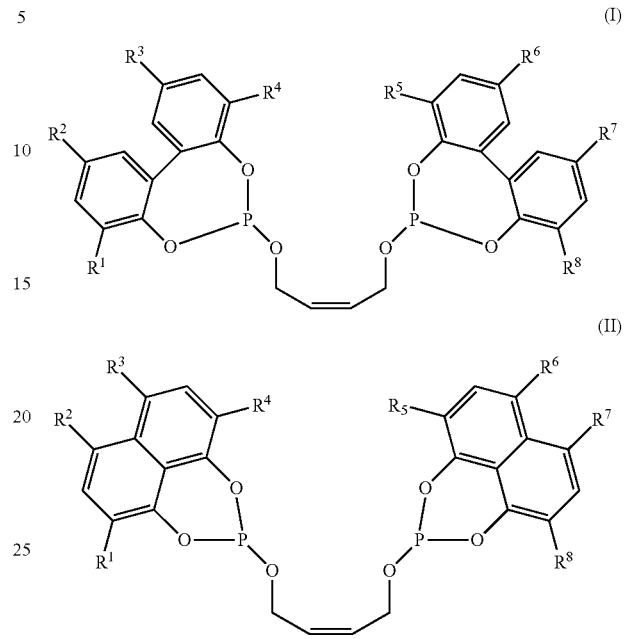

where $R^1$, $R^2$, $R^3$, $R^4$, $R^5$, $R^6$, $R^7$ and $R^8$ are selected from:
—H, —(C$_1$-C$_{12}$) alkyl or —O—(C$_1$-C$_{12}$) alkyl,
and the radicals $R^1$, $R^2$, $R^3$, $R^4$, $R^5$, $R^6$, $R^7$ and $R^8$ are not all simultaneously —$^t$Bu.

2. The compound according to claim 1, where $R^1$, $R^4$, $R^5$ and $R^8$ are selected from: —H or —(C$_1$-C$_{12}$) alkyl.

3. The compound according to claim 1, where the radicals $R^1$, $R^4$, $R^5$ and $R^8$ are not all simultaneously —$^t$Bu.

4. The compound according to claim 1, where the radicals $R^1$, $R^4$, $R^5$ and $R^8$ are not —$^t$Bu.

5. The compound according to claim 1, where at least one of the radicals $R^1$, $R^4$, $R^5$ and $R^8$ is —H.

6. The compound according to claim 1, where $R^2$, $R^3$, $R^6$ and $R^7$ are selected from: —H or —O—(C$_1$-C$_{12}$) alkyl.

7. The compound according to claim 1, where at least one of the radicals $R^2$, $R^3$, $R^6$ and $R^7$ is —H.

8. The compound according to claim 1, where the compound has the structure (I).

9. The compound according to claim 1, where the compound has the structure (I):

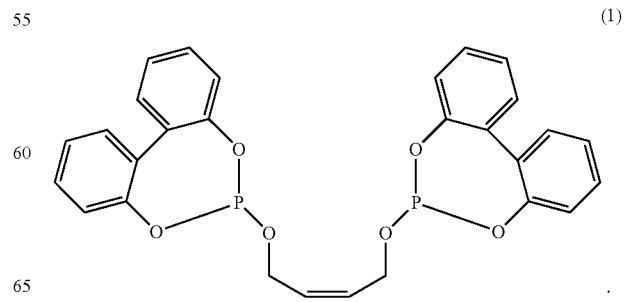

10. The compound according to claim 1,
where the compound has the structure (II).

11. The compound according to claim 1,
where the compound has the structure (2):

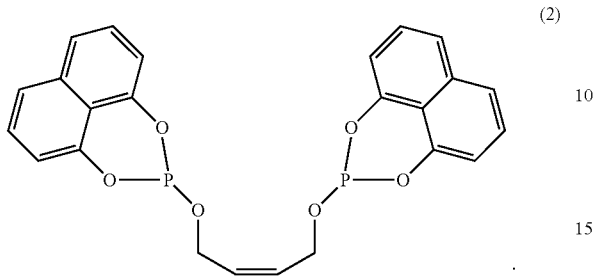

(2)

12. A ligand-metal complex comprising the compound according to claim 1 and a metal selected from: Rh. Ru, Co or Ir.

13. A process comprising the process steps of:
a) initially charging an olefin,
b) adding a compound according to claim 1 and a substance containing a metal selected from: Rh, Ru, Co or Ir,
c) feeding in $H_2$ and CO, and
d) heating the reaction mixture from steps a) to c), with conversion of the olefin to an aldehyde.

* * * * *